United States Patent [19]
Martin

[11] Patent Number: 5,641,623
[45] Date of Patent: *Jun. 24, 1997

[54] ELECTROCHEMILUMINESCENCE ASSAY

[76] Inventor: Mark T. Martin, 6516 Old Farm Ct., N. Bethesda, Md. 20852

[*] Notice: The term of this patent shall not extend beyond the expiration date of Pat. No. 5,643,713.

[21] Appl. No.: 368,429

[22] Filed: Jan. 4, 1995

[51] Int. Cl.$^6$ .................. C12Q 1/00; C12Q 1/34; G01N 33/554; G01N 33/53
[52] U.S. Cl. .................. 435/4; 435/7.32; 435/7.1; 435/7.2; 435/7.72; 435/18; 435/29; 435/34; 435/39; 424/1.69; 549/34
[58] Field of Search .................. 435/4, 7.32, 7.1, 435/7.2, 7.72, 18, 29, 34, 39; 424/1.1; 549/34

[56] References Cited

U.S. PATENT DOCUMENTS

| | | | |
|---|---|---|---|
| 3,905,871 | 9/1975 | Rubenstein et al. | 435/4 |
| 4,470,459 | 9/1984 | Copeland | 435/4 |
| 4,725,591 | 2/1988 | Matsuo et al. | 435/4 |
| 4,764,462 | 8/1988 | Bredehorst et al. | 435/18 |
| 5,057,302 | 10/1991 | Johnson et al. | 424/1.1 |
| 5,235,808 | 8/1993 | Taylor | 435/4 |
| 5,264,346 | 11/1993 | Chen | 435/4 |
| 5,310,687 | 5/1994 | Bard et al. | 435/4 |
| 5,321,143 | 6/1994 | Sharpless et al. | 549/34 |

FOREIGN PATENT DOCUMENTS

WO84/03303  8/1984  WIPO.

OTHER PUBLICATIONS

Yang et al., "Electrochemiluminescence: A New Diagnostic and Research Tool", 12 Bio/Technology, 193–194 (Feb. 1994).

Massey, Biomedical Products, "Electrochemiluminescence: A novel detection system . . . ", Oct. 1992 (not currently available).

Blackburn et al., "Eletrochemiluminescence Detection for Development . . . ", 37/9 Clin.Chem, 1534–1539 (1991) Publication Month not available. Please print Feb. 2, 1997.

Payne D.J. "Metallo–B–lactamaese —a new therapeutic challenge", 39 J. Med. Micro, 93–99 (1993) Publication month not available.

Coulton S. & Francois, I., "B–Lactamases: Targets for Drug Design", 31 Prog. Med. Chem., 297–349 (1994) Pub month not available.

Neu, H.C., "The Crisis in Antibiotic Resistance" 257 Science, 1064–1072 (Aug. 11, 1992).

W.L. Baker, "Co–existence of B–lactamase and penicillin acylase in bacteria . . . " 73, No. 1 J. Appl. Bacteriol., 14–22 (1992) (Publication Month not available).

A.C. Peterson et al., "Evaluation of Four Qualitative Methods for Detection of B–lactamase . . . " 8, No. 11 Eur. J. Clin. Microbiol. Infect. dis., 962–967 (1989) (Publication month not available).

Robert H. Yolken et al., "Rapid Diagnosis of Infections Caused by B–lactamase–Producing Bacteria . . . " 97, No. 5 The Journal of Pediatrics, 715–720 (Nov. 1980).

*Primary Examiner*—John Kight
*Assistant Examiner*—Louise Leary
*Attorney, Agent, or Firm*—John W. Ryan; Patrick J. Igoe; Thomas G. Wisemen

[57] ABSTRACT

A rapid single step assay suitable for the detection or quantification of β-lactam antibiotics and β-lactamases. The assay can be performed directly on samples of food, such as milk and meat, blood or serum and is useful in determining the suitability of a particular antibiotic in treating a particular bacterial infection and in diagnosis of a bacterial infection. The assay is also useful in determining and quantifying β-lactam antibiotic resistance. The assay can be performed on an IGEN Origen$^R$ Analyzer.

31 Claims, 7 Drawing Sheets

ELECTROCHEMILUMINESCENCE ASSAY

FIELD OF THE INVENTION

The present invention relates to the development of an electrochemiluminescence (ECL) based assay for the detection and the quantitative measurement of β-lactams and β-lactamases which assay is suitable for the diagnosis and the monitoring of the treatment of bacterial infections.

BACKGROUND OF THE INVENTION

Assays based on ECL are well known in the art and are finding expanding applications because of their accuracy, ease of use and freedom from radioactive materials.

A particularly useful ECL system is described in a paper by Yang et al, *Bio/Technology*, 12, pp. 193–194 (Feb. 1994). See also a paper by Massey, *Biomedical Products*, October 1992 as well as U.S. Pat. Nos. 5,235,808 and 5,310,687, the contents of these papers and patents being incorporated herein by reference.

ECL processes have been demonstrated for many different molecules by several different mechanisms. In Blackburn et al (1991) *Clin. Chem.* 37/9, pp. 1534–1539, the authors used the ECL reaction of ruthenium (II) tris (bipyridyl), $Ru(bpy)_3^{2+}$, with tripropylamine (TPA) (Leland et al (1990) *J. Electrochem. Soc.* 137: 3127–31) to demonstrate the technique. Salts of $Ru(bpy)_3^{2+}$ are very stable, water-soluble compounds that can be chemically modified with reactive groups on one of the bipyridyl ligands to form activated species with which proteins, haptens, and nucleic acids are readily labeled. The activated form of the Ru $(bpy)_3^{2+}$ used by Blackburn et al was $Ru(bpy)_3^{2+}$—NHS ester:

Beta-lactamases which hydrolyze the amide bonds of the β-lactam ring of sensitive penicillins and cephalosporins are widely distributed amongst microorganisms and play a role in microbial resistance to β-lactam antibiotics. Beta-lactamases constitute a group of related enzymes which are elaborated by a large number of bacterial species but not by mammalian tissues and can vary in substrate specificities. See generally Payne, D. J., *J. Med. Micro* (1993) 39, pp. 93–99; Coulton, S. & Francois, 1., *Prog. Med. Chem.* (1994) 31, 297–349; Moellering, R. C., Jr., *J. Antimicrob. Chemother.* (1993) 31 (Suppl. A), pp. 1–8; and Neu, H. C., *Science* (1992) 257, pp. 1064–1072.

The detection of β-lactamase activity in a body fluid has long been considered to be indicative of a recent or current bacterial infection.

The developing microbial resistance to antibiotics such as penicillin and cephalosporin has been of concern for awhile. Recently, this concern has escalated in light of the dwindling number of new antibiotics and the over-use of those which are known. It is becoming more imperative to select the optimum antibiotic for treating a particular infection and to avoid prescribing the latest antibiotic when effective alternatives exist. This ability to select the optimum antibiotic is especially critical in those facilities involved in long-term care facilities where antibiotic resistance is increasingly becoming a problem. The lifetime of the current family of antibiotics can be prolonged by the selection of the optimum antibiotic. See generally Harold C. Neu, "The Crisis in Antibiotic Resistance", Science Vol. 257 (Aug. 11, 1992) pp. 1064–1072.

The rising resistance to microbial resistance to antibiotics has heightened the need for a test which can rapidly measure quantitatively the degree of resistance to a particular β-lactam antibiotic such as a penicillin or a cephalosporin and then select the most appropriate antibiotic for a particular infective condition.

Several methods currently exist for the detection of microbial β-lactamases. Some representative examples follow.

W. L. Baker, "Co-existence of β-lactamase and penicillin acylase in bacteria; detection and quantitative determination of enzyme activities", *J. Appl. Bacteriol.* (1992) Vol. 73, No. 1, pp. 14–22 discloses a copper-reducing assay for the detection of penicilloates and a fluorescamine assay to detect 6-aminopenicillanic acid concentrations when both substances were produced by the action of the enzymes on a single substrate.

U.S. Pat. No. 5,264,346 (Nov. 23, 1993) discloses a colorimetric assay for β-lactamase which has a variety of applications. The assay is based on the decolorization of a chromophore formed by oxidation of either the N-alkyl derivative of p-phenylenediamine or the 3,3',5,5'-tetraalkyl derivative of benzidine. The decolorization is attributed to the presence of an open β-lactam ring product resulting from the hydrolysis of cephalosporin or penicillin. Decolorization with the open β-lactam product of penicillin requires the presence of a decolorization enhancer such as mercury containing compounds. The enhancer is not required for decolorization with the open β-lactam product of cephalosporin.

U.S. Pat. No. 4,470,459 (Sep. 11, 1984) discloses a rapid method for the detection of the presence of β-lactamase from microbial sources which is based on a β-lactamase conversion of a β-lactam substrate which reverses its ability to fluoresce. Specific β-lactams mentioned as having this property include ampicillin, cephalexin, amoxicillin, cefadroxil and cephaloglycin. The change in the ability to fluoresce is attributed to the presence of β-lactamase.

WO 84/03303 (Aug. 30, 1984) discloses a microbiological test process for identifying producers of β-lactamase. The assay relies on changes in acidity which affect the fluorescence of the indicator such as coumarin. This change in acidity is attributed to the conversion product produced by the presence of the β-lactamase.

A. C. Peterson et al, "Evaluation of four qualitative methods for detection of β-lactamase production in Staphylococcus and Micrococcus species", *Eur. J. Clin. Microbiol. Infect. Dis.* (1989), Vol. 8, No. 11, pp.962–7 presents certain factors which were employed in evaluating qualitative assays for β-lactamase.

Robert H. Yolken et al, "Rapid diagnosis of infections caused by β-lactamase-producing bacteria by means of an enzyme radioisotopic assay", *The Journal of Pediatrics*, Vol. 97, No. 5 (Nov. 1980) pp. 715–720 discloses a sensitive enzymatic radioisotopic assay for the measurement of β-lactamase as a rapid test for detection of bacterial infection. The assay protocol involves an incubation step with sample followed by the separation step on a positively charged column such as DEAE-Sephacel prior to measurement of the radioactivity of eluted fractions. The β-lactamase converted penicillinic product has an additional carboxyl group which insures its stronger binding to the positively charged column than the penicillin. Differences in radioactivity between the eluted fractions and the original values are attributed to the presence of β-lactamase.

Prior to the invention disclosed herein, there remains a need for a universal assay for β-lactams and β-lactamases which is both very rapid (10 minutes or less) and also very sensitive.

The invention disclosed within this application achieves these needs by adapting electrochemiluminescence methodologies to the measurement of β-lactams or β-lactamases. Other objects of the invention will also be apparent from the description of the invention which follows.

SUMMARY OF THE INVENTION

Broadly stated, the invention contemplates an electrochemiluminesence based assay for the detection of β-lactamases or β-lactam moieties. The invention has as one of its objects an universal assay for β-lactam antibiotics as well as β-lactamases which are both rapid (10 minutes or less) and sensitive (low micromolar concentrations of antibiotics and picomolar concentrations of β-lactamases). The assay would be suitable for the detection as well as the quantification of the β-lactam antibiotics and β-lactamases.

Central to use of electrochemiluminesence methodology as a measuring system for B- lactamases and β-lactams was the recognition by applicants that β-lactam antibiotics and/or their hydrolysis products will cause $Ru(bpy)_3^{2+}$ to emit light in the ECL instrument. Moreover, with all β-lactams tested, there is a substantial difference between intact antibiotics and their hydrolysis products in this ability. Accordingly, a change in chemiluminescence correlates with the presence of β-lactamase activity.

Equally surprising to applicants was the versatility of the assay to the measurement of various β-lactam structures and thereby the β-lactamase family of enzymes. Critical to this is the conversion of the tertiary amine structure of the intact antibiotic structure to the structure of the secondary amine in the hydrolyzed product. The hydrolyzed and/or unhydrolyzed compound functions as tripropyl amine in the prior art chemiluminescent assays.

All that is required is to incubate the sample with β-lactam antibiotic of interest and to measure the change in chemiluminescence over time using established protocols and apparatus. What was also not expected by applicants at the time was the quality of the results achievable in a relatively short time (5 minutes to 2 hours) and the sensitivity achieved for both the β-lactam and β-lactamases. As evidenced in Table I on p. 264 by Downey et al., "Chemiluminescence Detection Using Regenerable Tris (2, 2'bypyridyl) ruthenium (II) Immobilized in Nafion", Anal. Chem. 64 (1992) pp 261–268, there was no appreciation prior to this invention that the hydrolized structure of penicillin produced appreciable amounts of ECL.

DESCRIPTION OF THE DRAWINGS

Figure Legends:

FIG. 3 shows the quantitation of antibiotic hydrolysis using spectrophotometric (black bars) and ECL (gray bars) assay methods. As detailed in the text, the spectrophotometric methods varied depending on factors relating to unique characteristics of the electronic absorbance spectra of the unhydrolyzed and unhydrolyzed antibiotics, while a single ECL instrument method was used for all antibiotics. In all cases, 1.0 mM of each antibiotic was incubated at room temperature for 10 minutes with one of four enzymes.

FIG. 4: Standard curves of hydrolyzed and unhydrolyzed β-lactam concentration versus ECL. Figure A shows enzyme-catalyzed (*B. cereus*) β-lactamase hydrolysis of ampicillin. Figure B shows NaOH hydrolysis of cefoxitin. In both A) and B) the closed circles represent the intact antibiotic and the open circles represent the products of antibiotic hydrolysis. Samples were treated and analyzed as described in the legend for FIG. 3.

FIG. 5 shows quantitation of bacterial cells by ECL measurement of their β-lactamase activity. Various amounts of *E. coli* extract (centrifugation pellet) were incubated overnight in 1.0 mM ampicillin. In some cases, the β-lactamase inhibitor 6-β-Br-penicillanic acid was also added. Incubated mixtures consisted of 1.0 mM ampicillin and 0.1M sodium phosphate, pH 7.5 and either Amps *E. coli* (low levels of β-lactamase)(open triangles), Amps *E. coli* plus 6-β-Br-penicillanic acid (closed triangles), AmpR *E. coli* (high levels of β-lactamase) (closed circles), or AmpR *E. coli* plus 6-β-Br-penicillanic acid (open circles). To aliquots of the overnight-incubated samples was added $Ru(bpy)_3^{2+}$ and Triton X-100 to give final concentrations of 10 μM and 0.05%, respectively. ECL was measured using an IGEN ECL instrument.

DESCRIPTION OF PREFERRED EMBODIMENTS

Mechanism of ECL excitation is as follows. $Ru(bpy)_3^{2+}$ and antibiotic (hydrolyzed and/or unhydrolyzed) are oxidized at the surface of a gold electrode, forming $Ru(bpy)_3^{3+}$ and antibiotic$^+$·, respectively. In this description, antibiotic is either intact or hydrolyzed. The antibiotic$^+$· spontaneously loses a proton, forming antibiotic·. The antibiotic·, a strong reductant, reacts with $Ru(bpy)_3^{3+}$, a strong oxidant, forming the excited state of the detectant, $Ru(bpy)_3^{2+}$. The excited state decays to the ground state through a normal fluorescence mechanism, emitting a photon having a wavelength of 620 nm.

Organic compounds which are suitable electrochemical detectants include, for example, rubrene and 9,10-diphenyl anthracene. Many organometallic compounds are suitable electrochemical detectants, but of preferable use are Ru-containing compounds, such as ruthenium II tris-bipyridine chelate, and Os-containing compounds. Detectants useful in the presently disclosed invention can be found in U.S. Pat. 5,310,687 (May 10, 1994), the contents of which are incorporated herein by reference.

These detectants are stable for long periods. In addition, the detectants are safe and relatively inexpensive. They give a highly characteristic signal and do not occur in nature. Measurements based on luminescence of such detectants are sensitive, fast, reproducible and utilize simple instrumentation. The signal is generated repeatedly by each molecule of the detectant, thereby enhancing the sensitivity with which these detectants may be detected. The preferred electrochemiluminescent detectants of the present invention are conveniently referred to herein as $Ru(bpy)_3^{2+}$. Various amounts of this detectant, or its equivalent, may be employed. It is also to be noted that these detectants can be used directly in the biological or food samples without pretreatment of sample.

The energy necessary for formation of the excited state arises from the large difference in electrochemical potentials of the $Ru(bpy)_3^{3+}$ and the antibiotic·. The excited-state $Ru(bpy)_3^{2+}$ decays through a normal fluorescence mechanism, emitting a photon at 620 nm. This process regenerates the original form of the $Ru(bpy)_3^{2+}$, which is free to cycle multiple times through the reaction sequence. Each ECL-active detectant, therefore, can emit many photons during each measurement cycle, thereby enhancing detection.

Quantification of the $Ru(bpy)_3^{2+}$ detectant can be readily automated with relatively uncomplicated instrumentation. The heart of an instrument is the electrochemical flow-cell, containing the working electrodes and counter electrodes for initiation of the ECL reaction. Both of the electrodes are fabricated from gold, but other materials have been used with various degrees of success. A potentiostat applies various voltage waveforms to the electrodes, and a single photomultiplier tube (PMT) detects the light emitted during the ECL reaction. An Ag/AgCl reference electrode is placed in the fluid path downstream from the flow cell, and a peristaltic pump is used to draw various fluids through the flow cell. In a typical sequence, the assay fluid is drawn from a test tube into the flow cell and the detectant is quantified by applying a ramp voltage to the electrodes and measuring the emitted light. After the measurement, a high-pH cleaning solution is drawn into the cell for an electrochemical cleaning procedure. A conditioning solution is then drawn into the cell, and a voltage waveform is applied that leaves the surfaces of the electrodes in a highly reproducible state, ready for the next measurement cycle.

The ECL reaction can be efficiently initiated by many different voltage waveforms. Measurements of the working electrode current and the ECL intensity are induced by the application of a triangle wave to the electrodes. The applied voltage as shown is actually the voltage measured at the Ag/AgCl reference electrode and includes the effects of a significant uncompensated resistance; consequently, the actual voltage applied at the working electrode is substantially less than that depicted. The triangle waveform rises from 565 to 2800 mV at a rate of 750 mV/s and then decreases at the same rate to 1000 mV. The current that flows in the cell is primarily the result of the oxidation of the β-lactam antibiotic and the hydrolysis of water. Oxidation of both the β-lactam antibiotic and $Ru(bpy)_3^{2+}$ becomes evident when the applied voltage reaches ~1100 mV and produces a luminescence. The intensity of the luminescence increases with the applied voltage until the antibiotic at the surface of the electrode is depleted, resulting in decreased intensity. The intensity of the observed luminescence is great enough that it can easily be measured with conventional PMTs operating either in photon-counting or current modes.

The sample to which the β-lactam of interest has been added is then placed in a measuring cell to obtain an initial reading. Typically the β-lactam of interest is added in concentrations between 10 micromolar and 1.0 millimolar. The electrochemiluminescent detectant is typically present at $10^{-6}$M concentrations (range 1–15 μM). The sample containing cell is then incubated for a sufficient period of time to insure that β-lactamase catalyzed hydrolysis can occur if the enzyme is present. This period of time typically varies between 5 minutes and 2 hours. Longer and shorter periods of time are possible depending on sample and reagent concentrations. Since all that is involved is empirical parameters, their values can be determined using conventional techniques.

After incubation occurs, a second reading is taken. The difference in readings, if any, correlates with β-lactamase activity present in the sample. See FIG. 4 in this regard. In a similar fashion, a particular sample can be subdivided or a series of samples can be taken from a particular patient and sequentially treated with a series of β-lactam antibiotics to generate a profile for the sample or patient. This profile can be used by a physician to select a preferred antibiotic for treatment or be used to identify the microorganism involved based on an existing library of information. The preferred antibiotic for use in treating an infection is the one least hydrolyzed.

Also possible is the creation of a set of standards obtained by repeating the method above with a series of antibiotics using a β-lactamase from a series of representative β-lactamases. Such a representation is shown in FIGS. 3a–d. Values determined for an unknown can be compared against such a set for identification purposes. This information can be in electronic form to facilitate handling and comparison.

After the sample is treated with β-lactam antibiotic and/or incubated, the ECL measurement is performed by application of electrical potential to the working electrode. This gives a characteristic signal from the emitted light. Relatively little interference results from background presented by the other materials present in the sample or added buffer.

Accordingly, the apparatus and methodology suitable for the performance of the process of this invention include, as noted earlier, those shown in U.S. Pat. Nos. 5,068,088, 5,061,455, 5,093,268, and 5,147,806 and 5,221,605, which patents are expressly incorporated herein by reference. In addition, electrochemiluminesence molecules for use in the measuring system as detectants include those bidentate aromatic heterocyclic nitrogen-containing ligands of ruthenium and osmium described in U.S. Pat. No. 5,310,687 which patent are expressly incorporated herein by reference.

Reagent kits containing the materials necessary for the performance of the assays can be assembled to facilitate handling, and foster standardization. Materials to be included in the kit may vary depending on the ultimate purpose. Typically the kit would include the electrochemiluminescent detectant, necessary buffers, and standards. The standards can be chemical reagents or data (empirical) in printed or electronic form necessary for the calibration necessary for performance of the assay.

Example 1

ECL Assay of β-Lactam Hydrolysis by β-Lactamases

Figure 1:
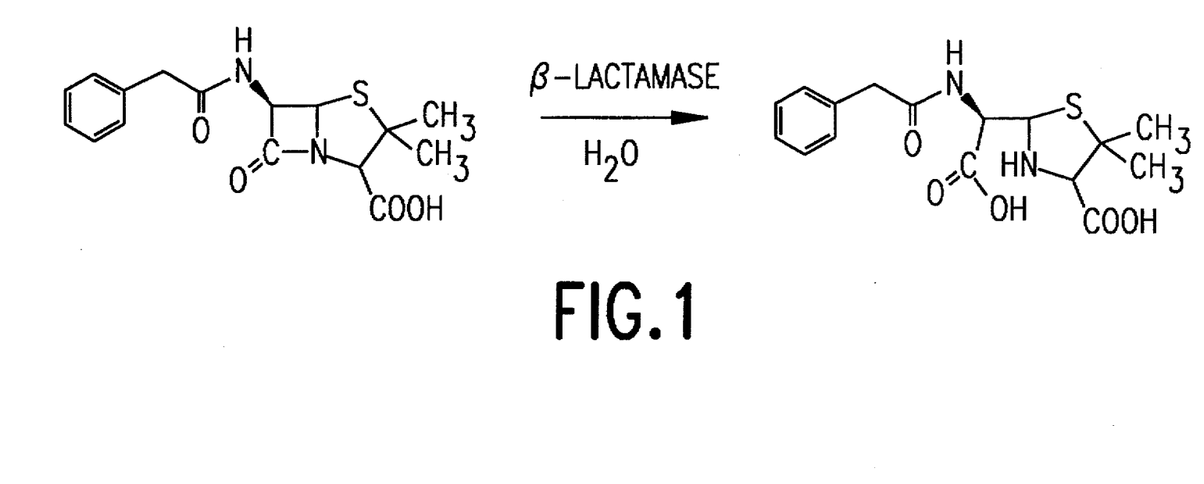
FIG. 1 illustrates β-lactamase-catalyzed hydrolysis of benzylpenicillin.

Bacterial β-lactamase enzymes hydrolyze and inactivate β-lactam antibiotic substrates (FIG. 1). There are over 100 β-lactamases produced by many different species of gram negative and gram positive bacteria (1). Each β-lactamase will hydrolyze a limited and unique "spectrum" of β-lactam antibiotics (for structures of some β-lactam antibiotics, see FIG. 2). Thus, if a β-lactamase-producing bacterial strain is challenged with an antibiotic that is not a substrate of its β-lactamase(s), the antibiotic may be lethal. Conversely, if a bacterial strain is challenged with a β-lactam antibiotic that is a substrate of its β-lactamase(s), that strain will destroy the antibiotic, resist the challenge, and survive. It is difficult to predict in advance whether a pathogenic microbe produces a β-lactamase and, if so, which antibiotics that particular enzyme recognizes and hydrolyzes. It would greatly benefit medical treatment of such microbial infections if, as part of the physician's decision-making process, a sample of a patient's infected tissue or biological fluid could be mixed with candidate antibiotics prior to antibiotic administration to determine whether a β-lactamase is present capable of hydrolyzing the antibiotic and rendering it ineffective.

Figure 2:
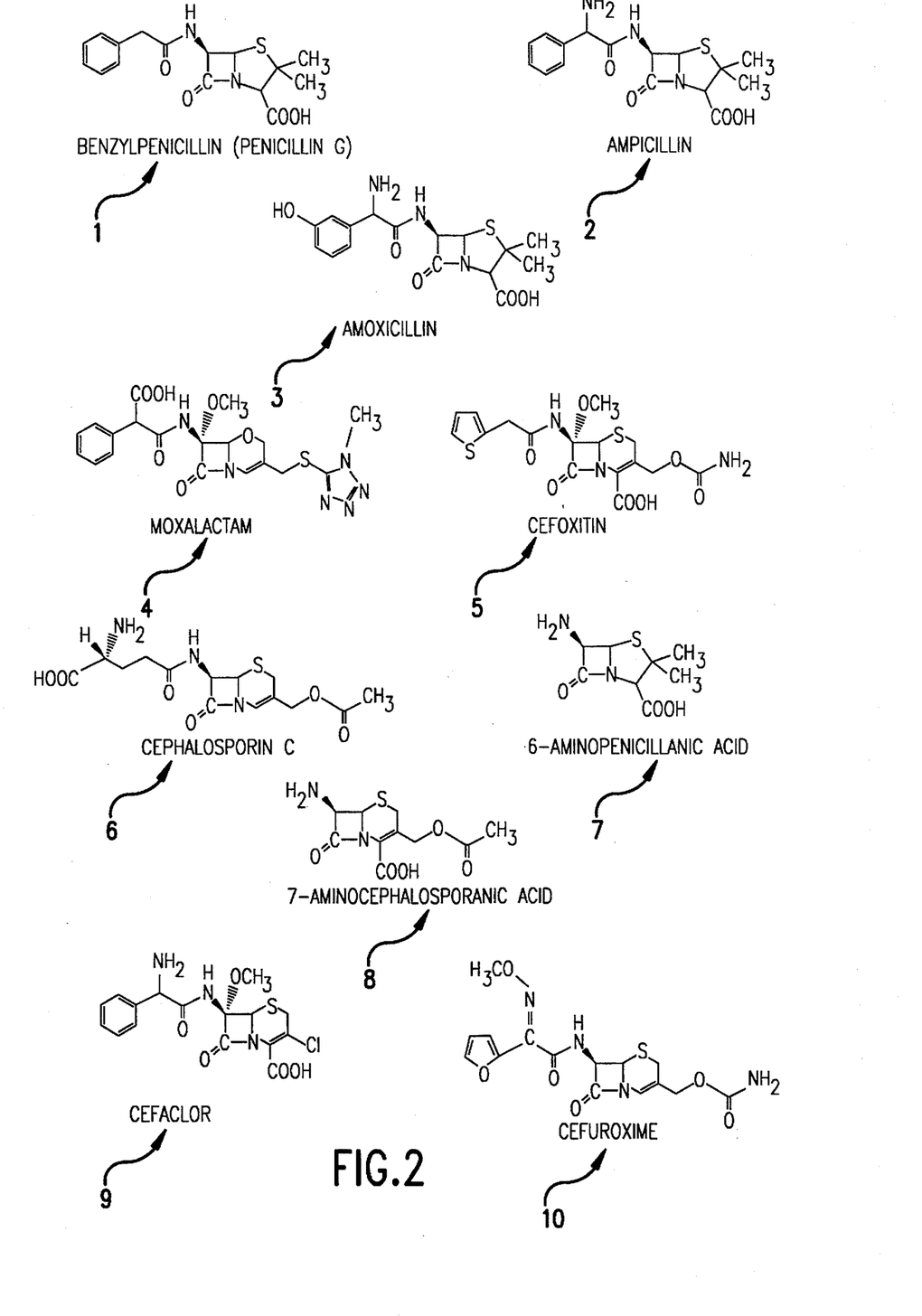
FIG. 2 shows chemical structures of some common β-lactams.
Figure 3A:
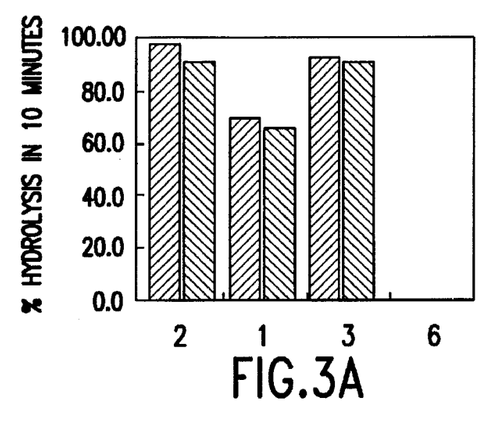
FIG. 3A shows *B. cereus* β-lactamase I (1.3 mM)
Figure 3B:
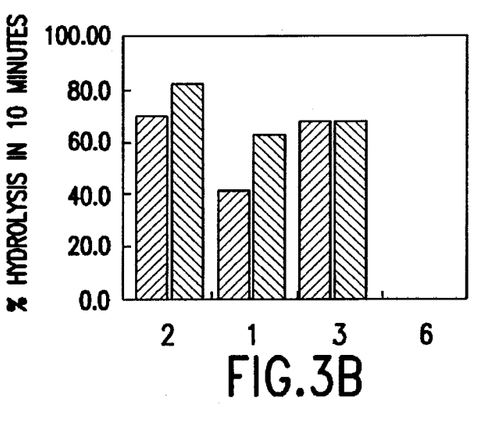
FIG. 3B shows *B. cereus* β-lactamase II (42.6 nM).
Figure 3C:
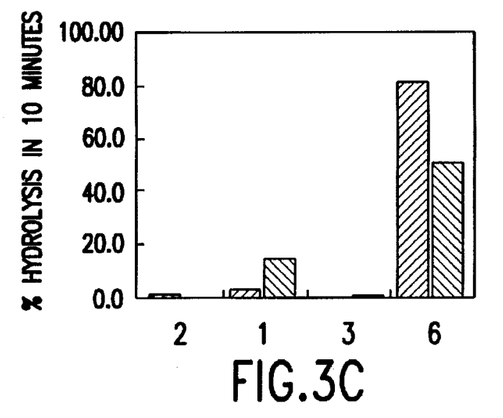
FIG. 3C shows *Enterobacter cloacae* P99 (1.9 nM).
Figure 3D:
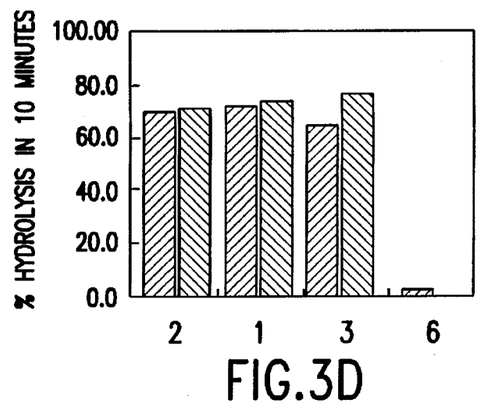
FIG. 3D shows *E. coli* RTEM (0.73 nM). For ECL experiments, 275 μL of each sample was mixed with 25 μL of 120 μM $Ru(bpy)_3^{2+}$ and 0.6% Triton X-100. The mixtures were analyzed using an ECL instrument (Origen[R] Analyzer, IGEN, Inc., Rockville, Md).

In one experiment, hydrolysis (or lack thereof) of six different commercially-obtained β-lactam antibiotics (benzylpenicillin, 1; ampicillin, 2; amoxycillin, 3; moxalactam, 4; cefoxitin, 5; and cephalosporin C, 6) by one or more of four different β-lactamases was detected and quantitated using an electrochemiluminescence (ECL)-based method. The antibiotics differ significantly in chemical structure, although each has in common the four-membered β-lactam ring (FIG. 2). Each antibiotic was dissolved to a concentration of 1.0 mM in a pH 7.5 solution of 0.1M phosphate (sodium salt) containing of 10 µM ruthenium (II) tris(bipyridyl) (abbreviated as Ru(bpy)$_3^{2+}$), and 0.05% Triton X-100. Other solutions of the antibiotics were made that were identical except that they also contained one of four commercially-obtained β-lactamase enzymes (either 1.3 nM Type I from *Bacillus cereus*, 42.6 nM Type II from *Bacillus cereus*, 0.73 nM RTEM from *E. coli*, or 1.9 nM *Enterobacter cloacae* P99). Following 10-minute incubations at room temperature (approximately 22° C.), ECL analyses of the antibiotic solutions (with and without each enzyme) were performed using an ECL-analyzing instrument (Origen$^R$ Analyzer, IGEN, Inc., Rockville, Md.). The effects of enzyme incubation on the ECL intensity were observed.

For verification of the source of generated ECL, hydrolysis of the same six antibiotics was also monitored spectrophotometrically (spectral changes are known to occur in the ultraviolet region upon hydrolysis of β-lactam antibiotics). Spectrophotometric analysis of antibiotic hydrolysis actually consisted of multiple methods because the UV spectral properties of the six antibiotics differ substantially. The wavelength monitored in each assay as well as the cuvette path length required individual optimization for each antibiotic; benzylpenicillin and ampicillin required a 10 mm cuvette and a wavelength of 240 nm, cephalosporin C required measurement a 2 mm cuvette and a wavelength of 260 nm, cefoxitin required a 2 mm cuvette and a wavelength of 265 nm, moxalactam required a 2 mm cuvette and a wavelength of 270 nm, and amoxicillin required a 2 mm cuvette and a wavelength of 240 nm. In contradistinction, ECL measurements were all made using identical ECL instrument settings.

The results, shown on FIGS. 3a–d, demonstrated that β-lactam hydrolysis by low (nanomolar or less) concentrations of β-lactamases can be detected by ECL in 10 minutes. Hydrolysis of the antibiotics moxalactam and cefoxitin are not shown in FIG. 3 because both ECL and spectrophotometric methods demonstrated that they were not catalyzed by any of the enzymes used in the experiment (although treatment with base showed that substantial ECL changes accompany hydrolysis of these compounds, see Example 2). FIG. 3 shows that quantitation of hydrolysis by spectrophotometric (black bars) and ECL (gray bars) assay methods give similar results. The results also demonstrate that each of the four enzymes tested has a unique "spectrum" of substrate specificity. Choice of a therapeutically-effective antibiotic in a clinical setting would favor one that is not significantly hydrolyzed by the microorganism's β-lactamase. Thus, this experiment can be thought of as a study of four "mock" infections. Each mock infection (enzyme) has been challenged with six candidate β-lactam antibiotics to determine β-lactamase substrate specificity, information that would assist in predicting each antibiotic's in vivo effectiveness.

Example 2

ECL Assay of Beta-Lactam Hydrolysis by Base

Beta-Lactam antibiotics can be hydrolyzed by acids or bases. Hydrolysis of β-lactam antibiotics with dilute sodium hydroxide generally yields experimentally identical ECL assay results as when they are hydrolyzed by β-lactamases (Table 1). In some cases where a particular β-lactam may not be recognized or hydrolyzed by any known β-lactamases, ECL quantitation of antibiotic can be made by comparison with the ECL characteristics of base-hydrolyzed samples of the antibiotic.

TABLE 1

Comparison of ECL of Penicillins Before and
After Hydrolysis by Base (NaOH) or Enzyme
(β-Lactamase)

| Antibiotic (1.0 mM) | Hydrolyzing Agent | Hydrol./Unhydrol. ECL (Ratio of ECL Counts) |
|---|---|---|
| Benzylpenicillin | Base | 18.0 |
| | Enzyme | 15.5 |
| Ampicillin | Bazse | 5.8 |
| | Enzyme | 5.3 |
| Amoxicillin | Base | 7.0 |
| | Enzyme | 5.5 |

Table 2 shows the effect of NaOH on the ECL generated by the 10 β-lactams whose structures are shown in FIG. 2.

TABLE 2

Effect of Base Hydrolysis on the ECL of
β-Lactams (antibiotic concentrations were approx.
1.0 mM)

| Beta-Lactam | Hydrol./Unhydrol. ECL Ratio |
|---|---|
| Moxalactam | 25.7 |
| Benzylpenicillin | 18.0 |
| Amoxicillin | 7.0 |

TABLE 2-continued

Effect of Base Hydrolysis on the ECL of
β-Lactams (antibiotic concentrations were approx.
1.0 mM)

| Beta-Lactam | Hydrol./Unhydrol. ECL Ratio |
| --- | --- |
| Ampicillin | 5.8 |
| 6-Aminopenicillanic acid | 5.4 |
| Cefaclor | 2.2 |
| Cefuroxime | 0.82 |
| Cephalosporin C | 0.40 |
| Cefoxitin | 0.38 |
| 7-Aminocephalosporanic acid | 0.33 |

Figure 6:
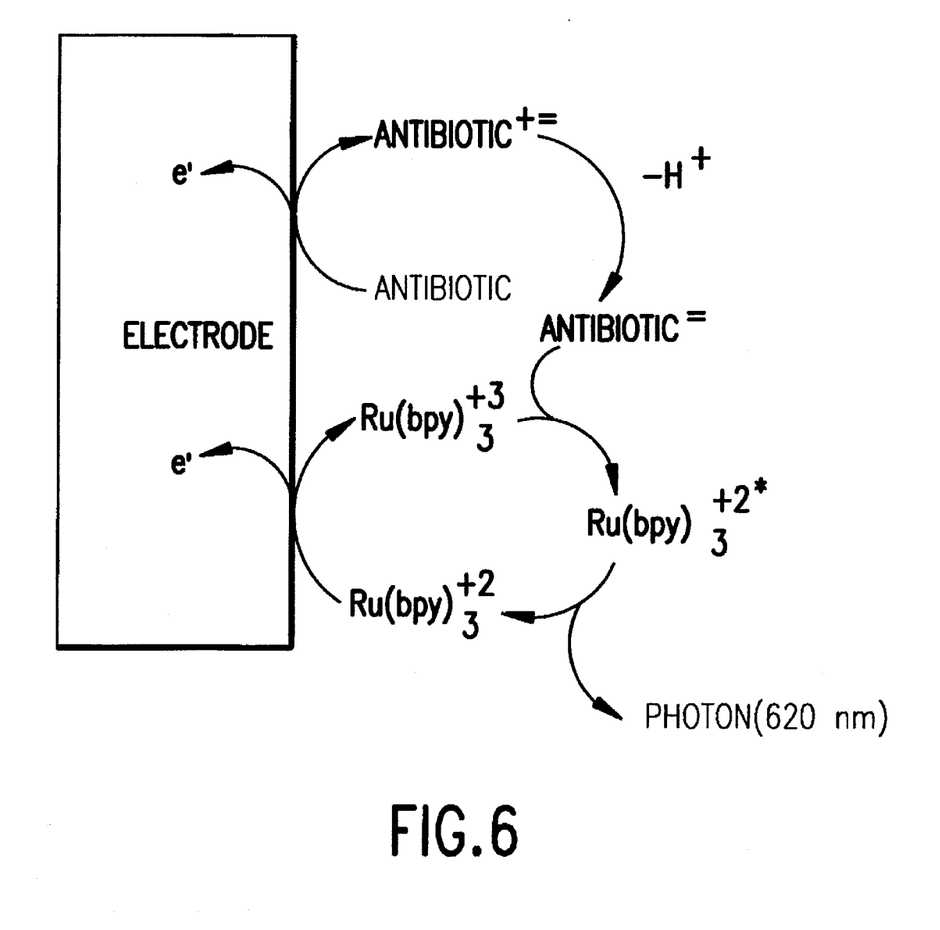
FIG. 6 illustrates a possible ECL reaction mechanism for antibiotics. In some cases, the hydrolysis product participates in this reaction to elicit light. However, in all cases tested, there is a substantial difference between a given antibiotic and its hydrolysis product.

Overnight treatment with 0.2M NaOH resulted in complete hydrolysis of the β-lactam ring in every case. It can be seen that in all instances base hydrolysis changes the ECL properties, although to varying extents. Some of the antibiotics tested (such as penicillin G, ampicillin, and amoxicillin) gave increased ECL after hydrolysis while others (such as cefoxitin and cephalosporin C,) gave substantially less ECL after hydrolysis. There is a general trend that penicillins give more ECL after hydrolysis and cephalosporins give less ECL after hydrolysis, although there are no obvious chemical structural reasons for this observation or for the fact that each compound behaves uniquely. The underlying mechanistic reasons for the differences in ECL behavior are probably a result of variations in the susceptibilities of the substrates and products of the reactions to form stable radical cations that can efficiently transfer an electron to $Ru(bpy)_3^{3+}$ (see FIG. 6 which shows a scheme of proposed ECL mechanism).

It should be noted that in some cases (with cephalosporin C and cefaclor), results varied depending on the concentration of NaOH used to hydrolyze the antibiotic and the length of hydrolysis time. This is believed to be due to other reactions, in addition to β-lactam hydrolysis, that occur between NaOH and these specific compounds. Enzymatic hydrolysis is a chemically milder way of hydrolyzing β-lactams and in some cases may be preferred to the use of NaOH.

Example 3

Quantitation of β-Lactams by ECL

Figure 4A:
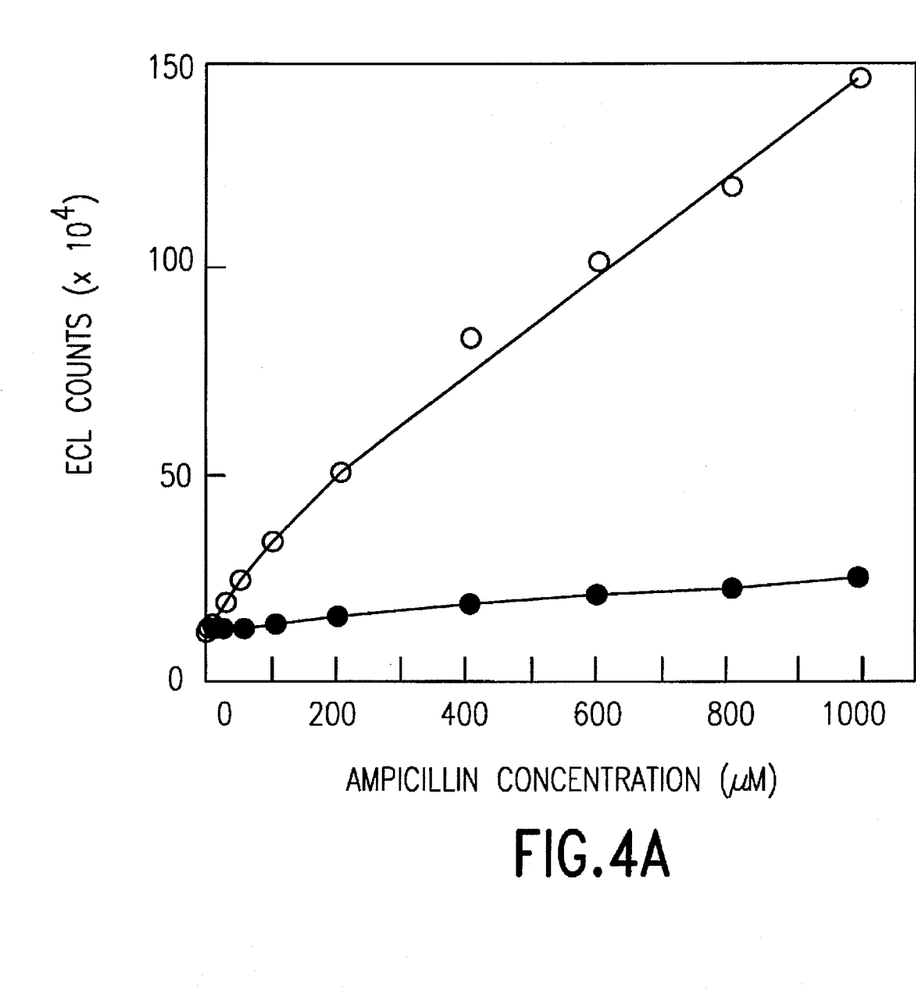
Figure 4B:
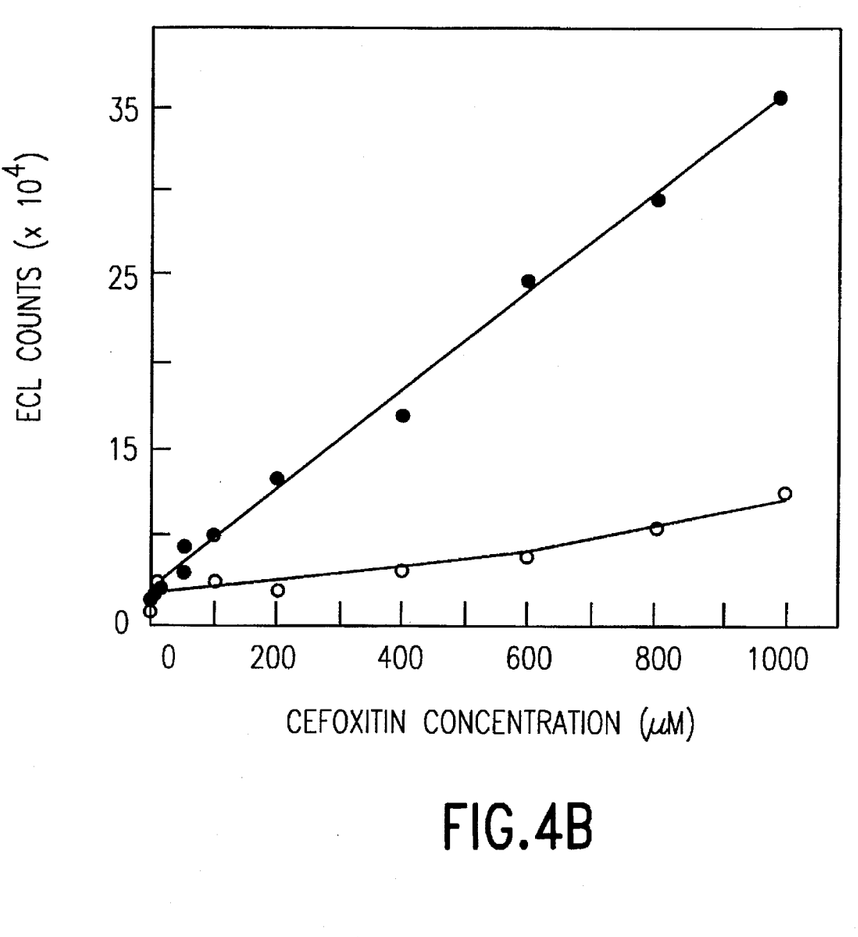

Determining the concentrations of β-lactam antibiotics is important in therapeutic drug monitoring and also in monitoring the quality of food such as meat and milk from cattle that have been administered antibiotics. For any analytical method, it is critical to show that the signal varies as a function of the analyte concentration. Detection and quantitation of β-lactams analyzed using ECL were found to be dependent on their concentrations such that the concentration of an unknown sample could be determined by comparison with an appropriate standard curve. Standard curves (antibiotic concentration vs. ECL) have been generated for penicillin G, ampicillin, amoxycillin, cefoxitin, cephalosporin C, and moxalactam. Shown in FIG. 4 are standard curves for the commonly-used penicillin, ampicillin, (FIG. 4a) and for the widely-used cephalosporin, cefoxitin (FIG. 4b). In the case of ampicillin, 275 µL of various concentrations of the antibiotic (0–1.0 mM) were incubated in 0.1M sodium phosphate, pH 7.5 for 10 minutes at room temperature in the absence or presence of 7 nM β-lactamase I from B. cereus (ampicillin). For cefoxitin, a 1.5 mM solution of the antibiotic was incubated in 0.2M NaOH overnight at room temperature. Appropriate dilutions (275 µL of 0–1.0 mM) of the solution of hydrolyzed cefoxitin and of a comparable unhydrolyzed solution of cefoxitin were made. To 275 µL of the ampicillin and cefoxitin solutions (hydrolyzed and unhydrolyzed) was added 25 µL of a solution of 120 µM $Ru(bpy)_3^{2+}$ and 0.6% Triton X-100 and the samples were analyzed in an IGEN Origen[R] ECL Analyzer. In general agreement with the data presented in Table 2 ampicillin hydrolysis resulted in an increase in ECL while cefoxitin hydrolysis caused a decrease in ECL. In both cases, a general trend was found that makes it possible to predict how much antibiotic would be present in a sample if the ECL was measured before and after appropriate hydrolysis.

Example 4

Quantitation of β-Lactamases by ECL

There are over 100 types of β-lactamase enzymes. Each has, under defined conditions of pH, temperature, and other factors, kinetic constants of substrate catalysis that are reproducibly characteristic of that particular enzyme. One kinetic constant that is especially important is the $k_{cat}$, defined as the maximum velocity ($V_{max}$) for catalysis of a given substrate per molecule of enzyme (for example, a $k_{cat}$ of 10 $s^{-1}$ means that one enzyme molecule will catalyze 10 substrate molecules per second at $V_{max}$). Thus, when an enzyme is operating at $V_{max}$ (which occurs when the substrate concentration is high), the enzyme concentration can be determined by measuring the rate of catalysis. Because many $k_{cat}$ values of β-lactamases with common β-lactam substrates are known, the concentration of a β-lactamase enzyme can be determined by measuring the rate of catalysis of a substrate at high substrate concentration (in units of product concentration formed per unit time). These types of measurements can be done using ECL.

For example, if one would like to quantitate the concentration of β-lactamase I from Bacillus cereus in a solution of defined pH, temperature and other factors, penicillin G could be added to give a sufficiently high concentration (such as 1.0 mM) so that the enzyme would operate at $V_{max}$. ECL measurements of penicillin turnover would be made at no fewer than two time points; for example at times=0, 1.0, 2.5, 5.0, 7.5, and 10.0 minutes after initiation of the enzyme-catalyzed reaction. By comparison of the ECL generated in a standard curve (concentration of hydrolyzed penicillin G vs. generated ECL), the initial rate of catalytic hydrolysis could be determined and this value would be the maximal velocity. Division of this experimentally-determined $V_{max}$ (for example, 2200 nM penicillin G hydrolyzed per second) by the literature-reported $k_{cat}$ value (for example, 2200 $s^{-1}$ (established in Martin, M. T. & Waley, S. G., Biochem. J. (1988) 254, pp. 923–925.) would give the enzyme concentration (1 nM).

Example 5

ECL Detection and Quantitation of β-Lactam Antibiotics in Biological Fluids Such as Blood, Serum, Urine, or Throat Swabs.

Detection of antibiotics in biological materials could be readily carried out following removal of any cells that might be present that could interfere with the ECL process or measurement. Cell removal can be carried out by well-known means such as filtration or centrifugation. The remaining fluid can then be measured for antibiotic-facilitated ECL as described elsewhere in this document. Two samples will be measured for ECL; one sample will be the patient's treated fluid, the other sample will be the same patient's fluid but containing an added β-lactamase enzyme known to hydrolyze that antibiotic will be measured for ECL (ECL will be measured following a sufficient incubation time for the enzyme to completely hydrolyze any antibiotic that may be present). The difference in ECL between the untreated and enzyme-treated samples will be indicative of the presence of the antibiotic and the extent of ECL difference will indicate the concentration of that antibiotic. A standard curve can be generated by adding to the fluid of the patient known amounts of the antibiotic and measuring ECL before and after enzyme-catalyzed hydrolysis. The standard curve should be generated using the same patient's fluid to which known concentrations of antibiotic have been added because the fluid may have substances in it which affect the ECL process or measurement that are unique to that particular patient.

Example 6

ECL Detection and Quantitation of β-Lactam Antibiotics in Food Such as Milk or Meat Detection of antibiotics in liquid foods such as milk can be carried out either directly on the liquid or after treatment to remove components such as lipids and proteins or other non-antibiotic substances that may interfere with the ECL process or measurement. Such removal steps are common laboratory procedures and may include high speed centrifugation (for example, 10,000 rpm in a standard laboratory centrifuge for 30 minutes). Centrifugation would cause a layer of solid fat to form on the surface of liquids such as milk. The layer of fat could be manually removed by using, for example, a spatula. Protein could be removed either by precipitation using ammonium sulfate or, preferably, by ultrafiltration. Ultrafiltration is a process of removing high molecular weight substances from liquids by pressurized filtration through a membrane containing defined nominal pore sizes (see Amicon catalog (Danvers, Mass.)) for ultrafiltration equipment and further information). In the case of antibiotics (which typically have molecular weights of less than 1000 Da), a membrane with a molecular weight cut-off of 10,000 Da might be best. Such membranes retain molecules with nominal molecular weight higher than 10,000 such that the filtrate would contain only low molecular weight (<10,000 Da) substances, including antibiotics. Higher molecular weight cut-off membranes (50,000–100,000 Da) might filter faster but would not retain as much potential ECL-interfering material.

Following any necessary treatments such as centrifugation and ultrafiltration, a defined volume of the liquid will then be measured for ECL by standard procedures described elsewhere in this document. An identical sample could be treated with a β-lactamase known to efficiently hydrolyze the β-lactam antibiotic suspected to be present in the liquid. Following sufficient time for hydrolysis (dependent on temperature, pH, and enzyme concentration) the second sample is measured for ECL. Since β-lactamases specifically hydrolyze β-lactam antibiotics but give little or no ECL at the low concentrations (typically nanomolar) required for catalysis, the difference in ECL between the hydrolyzed and non-hydrolyzed samples will be an indication of the β-lactam antibiotic concentration in the liquid. To quantitate the concentration of detected antibiotic, a standard curve could be generated using known amounts of the antibiotic suspected to be present (hydrolyzed and unhydrolyzed). In generating a standard curve, it is preferable to add the known antibiotic to the food such as milk and treat the liquid the same as the unknown solutions (for example, by centrifugation and ultrafiltration). Testing of the analyzed material for different antibiotics could be done by repeating this experiment on similar samples but using different β-lactamases which would each specifically hydrolyze different antibiotics. Such repetitive treatment with different enzymes could help to identify the antibiotics that are present in the liquid.

Detection of antibiotics in solid food such as meat could be carried out similarly except that the antibiotic would have to be extracted (solubilized) from the solid food. Initially, a sample of the food could be suspended in buffer (preferably 0.1M phosphate, pH 7.0) and minced in a blender until smooth. The antibiotic may be further extracted by sonication on ice which would disrupt any cells present, releasing any antibiotic present inside the cells. Following mincing and sonication, the material could be treated similarly to liquid food as described above. Namely, the material could be centrifuged and/or ultrafiltered. In the case of meat, centrifugation would primarily result in a pellet consisting of cellular debris (as opposed to milk in which centrifugation results in a surface fat layer). In generating standard curves, the known antibiotic should be added early in the process, preferably to the buffer used in mincing.

Beta-lactam antibiotics were detected in milk (Vitamin D Mil, Embassy Dairy, Waldorf, Md., Grade A pasteurized and homogenized). The following results were obtained for benzylpenicillin (300 μL total volume containing 250 μL milk, 10.0 μM Ru(bpy)$_3^{2+}$, 1.0 mM penicillin G, +/−18 nM β-lactamase I from *B. cereus*) and for cephalosporin C (300 μL total volume containing 250 μL milk, 10.0 μM Ru(bpy)$_3^{2+}$, 1.0 mM cephalosporin C, +/−18 nM β-lactamase P99 from *E. cloacae*).

| Sample | ECL Counts |
|---|---|
| Benzylpenicillin | |
| Milk + Ru(bpy)$_3^{2+}$ + penicillin | 1880 |
| Milk + Ru(bpy)$_3^{2+}$ + penicillin + enzyme | 10,100 |
| Cephalosporin C | |
| Milk + Ru(bpy)$_3^{2+}$ + cephalosporin C | 7960 |
| Milk + Ru(bpy)$_3^{2+}$ + ceph. C + enzyme | 9340 |

Similar experiments were carried out with antibiotics in milk hydrolyzed with NaOH;

| Sample | ECL Counts |
|---|---|
| Benzylpenicillin | |
| Milk + Ru(bpy)$_3^{2+}$ + penicillin | 19,100 |
| Milk + Ru(bpy)$_3^{2+}$ + Penicillin + NaOH | 64,400 |
| Cephalosporin | |
| Milk + Ru(byp)$_3^{2+}$ + cephalosporin C | 41,200 |
| Milk + Ru(bpy)$_3^{2+}$ + Ceph. C + NaOH | 35,100 |

As can be seen in the above tables for cephalosporin C, the effect of hydrolysis on the ECL depends on the method of hydrolysis; enzyme hydrolysis causes the counts to increase while NaOH hydrolysis causes the counts to decrease.

Appropriate control experiments showed that this is not a result of the presence of enzyme. As described elsewhere in this document, NaOH hydrolysis of this compound is unusually method dependent, a phenomenon suspected to result from the formation of alternative ECL-active hydrolysis products. The results are reproducibly consistent within any given method of hydrolysis. Other experiments with centrifugation of the milk to remove fat gave similar results for both benzylpenicillin and cephalosporin C. Standard curves showed that less than 25 μM benzylpenicillin and less than 250 μM cephalosporin C could be detected in milk using ECL.

Example 7

ECL Assay of β-Lactamases in Biological Materials Such as Blood, Urine, Serum or Throat Swabs The determination of β-lactamases in biological materials would be carried out in a method similar to that described in Example 4. In essence, a known antibiotic would be mixed with the biological fluid to a known concentration (for example 1.0 mM). An immediate ECL reading could be made and another reading could be made at some time later (it could be 5 minutes if the concentration of β-lactamase is relatively high or as long as overnight if the β-lactamase concentration is low). A change in ECL would indicate antibiotic hydrolysis by a β-lactamase. The extent of antibiotic turnover could be compared to a standard curve of antibiotic concentration hydrolyzed vs. ECL generated. As with measurement of antibiotics in biological fluids as described in Example 5, it may be advisable to treat the fluid by known means to remove any non-β-lactamase substances that may interfere with the ECL process or measurement. The enzyme present in a throat swab may need to be solubilized by addition of buffer.

Example 8

ECL Assay of β-Lactamases in Food Such as Milk and Meat

Detection and quantitation of β-lactamases in liquid (such as milk) or solid (such as meat) foods can be carried out using ECL. In the case of liquid foods, appropriate known methods may be required to remove non-β-lactamase substances that may interfere with the ECL process or measurement. For example, filtration through common filter paper may be useful in removing particulates from milk. Also, centrifugation of milk would remove lipids which might interfere with measurements. In the case of solid foods such as meat, homogenization in a Waring blender with added buffer (for example, 0.1M phosphate, pH 7.0) followed by sonication at 4° C. and centrifugation (10,000×g for 30 minutes) would aid in enzyme solubilization. Following these procedures, it might also be useful to add an ultrafiltration step to remove molecules of over 100,000 Da. The ultrafiltration filtrate will contain any β-lactamases which generally have molecular weights of about 30,000 Da. The ECL detection of β-lactamases in these food-derived solutions would consist of first adding a chosen β-lactam antibiotic (for example, penicillin G to a concentration of 1.0 mM) and making an immediate ECL measurement followed by at least one more measurement some later time(s) (the times could be as short as 5 minutes or as long as overnight). Any change in ECL with would indicate the presence of β-lactamase-catalyzed hydrolysis of the added antibiotic. The extent of hydrolysis could be determined by comparison with a standard curve (antibiotic concentration hydrolyzed vs. ECL) that has been generated under comparable conditions.

Example 9

ECL Assay of β-Lactamases in Bacterial Culture

It is preferable and sometimes essential to detect β-lactamases in a bacterial culture medium (such as in defined laboratory media or in blood, urine, or milk) without extensive isolation steps. In one application, in situ detection of β-lactamases in the blood of a patient infected with a pathogenic microbe could beneficially affect decisions regarding the medical treatment of that individual. In such an application, it may be prohibitively time-consuming or otherwise impractical to purify the β-lactamase in order to detect it. Thus, it is important to be able to detect β-lactamases in the presence of the microbe that produced it and in the culture medium in which the bacterium has grown.

Beta-lactamases are produced by both gram negative and gram positive bacteria. In the case of gram negative bacteria (e.g., E. coli), β-lactamases are sequestered in the periplasmic space. In gram positive bacteria (e.g., B. cereus), the enzyme is secreted into the medium surrounding the cell. It is valuable to be able to detect β-lactamase activity in both gram negative and gram positive bacterial cultures. Because the enzymes are present in physically different states (sequestered vs. secreted) in the two types of bacteria, β-lactamase detection may or may not require somewhat different experimental protocols.

Two strains of the gram negative bacterium, E. coli, were grown overnight at 30° C., each in 10 mL of LB culture medium. One strain, is called E. coli AmpR (ATCC; DH5αFIQpDsubE$_c$F4) because it is resistant to ampicillin due to production of β-lactamases. The other strain, termed E. coli Amps (ATCC;Jm105), does not produce high levels of β-lactamase and was used as a control (ampicillin-sensitive) strain. The cells were isolated from the culture medium as a centrifugation pellet by centrifugation at 2800 rpm in a Sorvall RT 6000D centrifuge followed by removal of the supernatant solution by decanting. Tests were conducted with the decanted supernatant but, at least with E. coli, much more β-lactamase activity was detected in the pellet. The pelleted cells were resuspended in 9.5 μL of 50 mM Tris-acetate buffer, pH 8.0, then sonicated for 15 minutes in an ice-chilled beaker. Typically, portions of the resulting suspension (9.5–10.0,μL) were added to 300 μL of 0.1M phosphate buffer, pH 7.5 containing 500 μM ampicillin, 10.0 μM Ru(bpy)$_3^{2+}$, and 0.05% Triton X-100. After various incubation times (none—overnight), the suspensions were tested for their ability to generate electrochemiluminescence using an IGEN ECL Analyzer. In some cases, 5.0 μL of a 1.0 mM solution of the β-lactamase inhibitor, 6-β-Br-penicillanic acid, was added as a control of the source of generated ECL.

A similar protocol was used with the gram negative bacterium, B. cereus. One strain secretes a relatively high amount of β-lactamase (termed B. cereus AmpR) (ATCC; 27348) and the other strain secretes little β-lactamase (termed B. cereus AmpS)(ATCC; 9139). The growth conditions and experimental procedures were identical as described above for E. coli except that in some cases, as will be described below, the supernatant solution was used for the ECL experiments.

The results for E. coli showed that β-lactamase activity associated with cell cultures could indeed be measured by using ECL without extensive purification. After a 1.0-hour incubation of E. coli samples with 500 μM ampicillin solutions, the following ECL results were obtained:

TABLE 3

ECL Detection of β-Lactamase Activity in *E. coli*

| Sample | ECL Counts |
| --- | --- |
| *E. coli* AmpS + Ru(bpy)$_3^{2+}$ + ampicillin | 36,400 |
| *E. coli* AmpR + Ru(bpy)$_3^{2+}$ + ampicillin | 106,000 |
| *E. coli* AmpS + Ru(bpy)$_3^{2+}$ + 6-β-Br-penicillanic acid + ampicillin | 35,000 |
| *E. coli* AmpR + Ru(bpy)$_3^{2+}$ + 6-,B-Br-penicillanic acid + ampicillin | 36,700 |

These data demonstrate that β-lactamase activity can be detected in situ in gram negative bacteria. Similar results were obtained with the gram positive bacterium *B. cereus*, but using the centrifugation supernatant rather than the pellet. Once again the results were obtained after a 1.0-hour incubation with 500 µM ampicillin.

TABLE 4

ECL Detection of β-Lactamase Activity in *B. cereus*

| Sample | ECL Counts |
| --- | --- |
| *B. cereus* AmpS + Ru(bpy)$_3^{2+}$ + ampicillin | 33,600 |
| *B. cereus* AmpR + Ru(bpy)$_3^{2+}$ + ampicillin | 47,200 |
| *B. cereus* AmpS + Ru(bpy)$_3^{2+}$ + 6-β-Br-penicillanic acid + ampicillin | 25,600 |
| *B. cereus* AmpR + Ru(bpy)$_3^{2+}$ + 6-β-Br-penicillanic acid + ampicillin | 22,500 |

These results demonstrate that β-lactamase secreted by gram positive cells can be detected in one hour by ECL.

Figure 5:
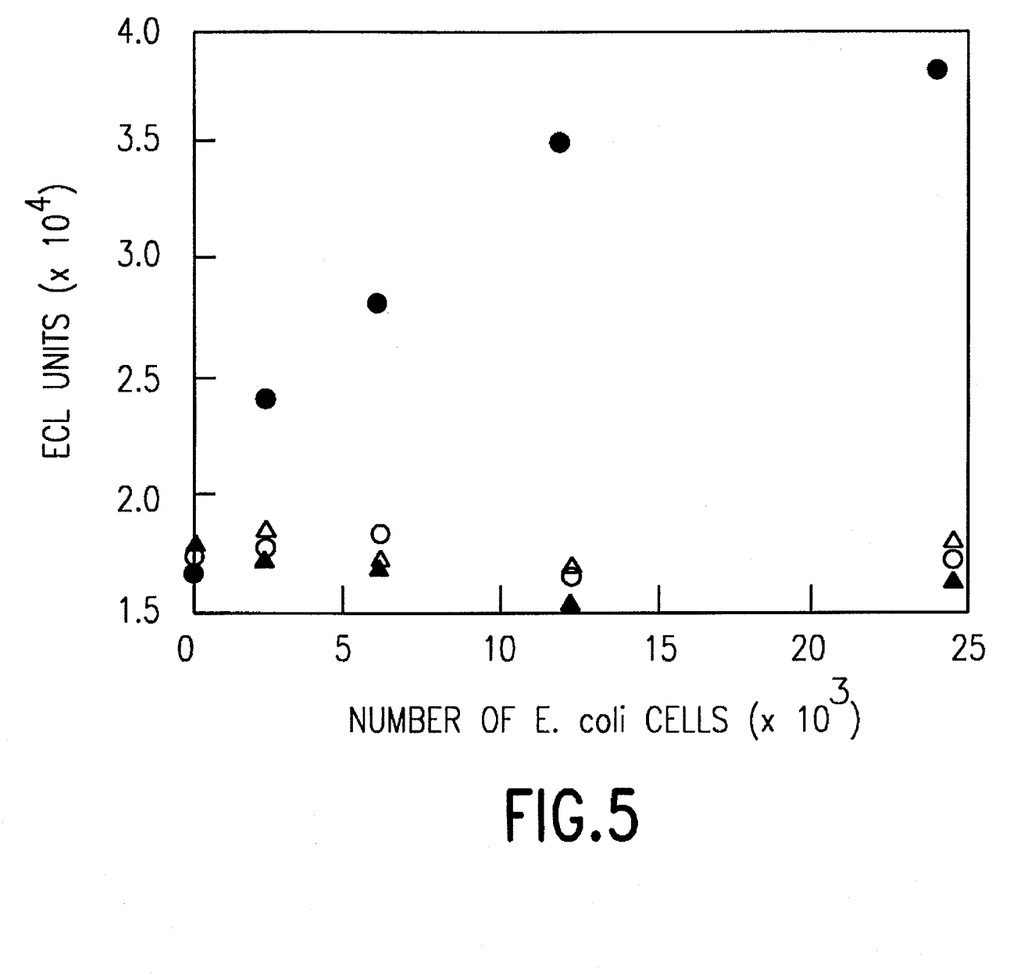

In some applications, rapid detection of β-lactamases may not be as critical as the detection of a small number of bacterial cells that may be present in a sample. Experiments were carried out to determine the lowest number of cells detectable by their β-lactamase activity under the conditions used. Using cultures of *E. coli* grown overnight in standard (LB) growth media, increasingly greater dilutions of culture centrifugation pellets were tested by overnight incubations with ampicillin in a similar methodology as described above. *E. coli* concentrations in cell culture were determined by spectrophotometric absorbance at 600 nm and subsequent comparison to absorbances of plated cultures. As seen in FIG. 5, the lower detection limit of *E. coli* cells in an overnight incubation was 2440.

Example 10

Identification of Bacteria by ECL Assay of Their Beta-Lactamases

There are many different types of β-lactamase enzymes. The structures (amino acid sequences) can differ substantially between enzymes as well as their substrate specificities. Because there are many different β-lactam antibiotics and many different β-lactamases, almost all β-lactamases can in theory be identified by the relative extent of hydrolysis of a series of different β-lactam antibiotic substrates (that is by its individual "spectrum" of substrate specificity). A given bacterial strain could be identified by its unique β-lactamase substrate specificity (see FIGS. 3a–d). In identifying a given unknown bacterial strain, appropriately-treated aliquots of that strain (pellet or supernatant as described in Example 9) could be mixed with a series of appropriately diverse antibiotics (including both cephalosporins and penicillins). After an appropriate length of time (from 5 minutes to overnight), the ECL of the different incubation mixtures could be read and compared with appropriate standards to determine relative rates of turnover of the different antibiotics from 0–100% turnover is expected depending on the enzyme concentration and the individual antibiotic/enzyme pair). Based on known substrate specificities for known bacterial strains, the bacterial species in question could be identified.

Although the examples illustrate various modifications of the present invention, other variations will suggest themselves to those skilled in the art in light of the above disclosure. It is to be understood, therefore, that changes may be made in the particular embodiments described above which are within the full intended scope of the inventions as defined in the appended claims.

What is claimed is:

1. A kit for measuring β-lactam antibiotics or β-lactamases comprising premeasured amounts of a bidentate aromatic heterocyclic nitrogen-containing ligand of ruthenium or osmium reagent and a β-lactam or lactamase standard wherein the premeasured amounts are sufficient to perform a single sample measurement.

2. The kit according to claim 1 wherein the kit contains a series of containers having the premeasured amounts of reagents within them.

3. The kit according to claim 2 wherein the series of containers are prepared for use in an automated assay.

4. The kit according to claim 1 wherein the standard is a β-lactam standard.

5. The kit according to claim 1 wherein the standard is a β-lactamase standard.

6. The kit according to claim 4 or 5 wherein the beta-lactam or beta-lactamase standard is a known amount of beta-lactamase or beta-lactam, respectively.

7. The kit according to claim 1 wherein the standard is a profile of microbial resistance to β-lactam antibiotics.

8. The kit according to claim 1 wherein the standard is a profile of β-lactam substrate specificities for known β-lactamases.

9. The kit according to claim 1 wherein the bidentate aromatic heterocyclic nitrogen-containing ligand of ruthenium is Ru(bpy)$_3^{2+}$.

10. A method for measuring the presence of β-lactamase comprising, (a) contacting a sample suspected of containing β-lactamase with a β-lactam and a bidentate aromatic heterocyclic nitrogen-containing ligand of ruthenium or osmium reagent;

(b) subjecting the contacted sample of step (a) to conditions which result in electrochemiluminesence;

(c) measuring the resulting electrochemiluminescence to obtain a reading;

(d) incubating the mixture;

(e) subjecting the incubated mixture of step (d) to conditions which result in electrochemiluminesence; and (f) measuring the resulting chemiluminescence and comparing it to the previously measured value to determine the difference, if any, in the measured values thereby indicating the presence of β-lactamase.

11. The method of claim 10 wherein the sample is a biological material is selected from urine, pus, secretions, throat swab, blood or serum.

12. The method of claim 10 further comprising,
   (g) comparing the difference with a standard value to determine the amount of β-lactamase present in the sample.

13. A method for measuring the presence of β-lactam comprising,
   (a) contacting a sample containing β-lactam with a β-lactamase and a bidentate aromatic heterocyclic nitrogen-containing ligand of ruthenium or osmium reagent;
   (b) subjecting the contacted sample of step (a) to conditions which result in electrochemiluminesence;
   (c) measuring the resulting electrochemiluminescence to obtain a reading;
   (d) incubating the mixture;
   (e) subjecting the incubated mixture of step (d) to conditions which result in electrochemiluminesence;
   (f) measuring the resulting chemiluminescence and comparing it to the previously measured value to determine the presence of a difference in measured values; and
   (g) comparing the difference with a standard value to determine the quantitative amount of β-lactam present in the sample.

14. The method of claim 13 wherein the sample is a biological material selected from urine, pus, secretions, food, blood, throat swab or serum.

15. The method of claim 12 or 13 wherein performance of the steps is automated.

16. The method of claim 13 wherein the steps are performed on a sample contained in a single container.

17. The method of either claim 10 or 13 wherein the method is performed in the absence of an added radical-forming reductant reagent.

18. The method according to claim 17 wherein the reductant reagent is tripropylamine (TPA).

19. The method of claim 10 or 13 wherein the beta-lactam or beta-lactamase standard is a known amount of beta-lactamase or beta-lactam, respectively.

20. The method of claim 10 or 13 wherein the standard is an electronic record.

21. The method of claim 10 or 13 wherein the bidentate aromatic heterocyclic nitrogen-containing ligand of ruthenium or osmium is Ru(bpy)$_3^{2+}$ reagent or OS(bpy)$_3^{2+}$ respectively.

22. The kit according to claim 1 wherein the β-lactam substrate is selected from the group consisting of benzylpenicillin, ampicillin, amoxycillin, moxalactam, cefoxitin, and cephalosporin.

23. The kit according to claim 1 wherein the β-lactamase is selected from the group consisting of *Bacillus cereus* Type I β-lactamase, *Bacillus cereus* Type II β-lactamase, *E. coli* RTEM β-lactamase and *Enterobacter cloacae* P99 β-lactamase.

24. The kit according to claim 1 wherein the β-lactam substrate is selected from the group consisting of cephalosporin, cefoxitin, moxalactam, and amoxicillin.

25. The kit according to claim 1 wherein the β-lactam substrate is selected from the group consisting of 6-aminopenicillanic acid, cefaclor, cefuroxime, cefoxitin, 7-aminocephalosporanic acid, penicillin G, ampicillin, amoxicillin, and cephalosporin C.

26. The kit according to claim 1 wherein the β-lactam substrate is selected from the group consisting of penicillin G, ampicillin, amoxycillin, cefoxitin, cephalosporin C, and moxalactam.

27. A kit according to claim 1 for identifying β-lactams which comprises a sufficient number of unit dosage amounts of different β-lactamases to empirically generate a hydrolysis pattern spectrum, and corresponding premeasured amounts of a bidentate aromatic heterocyclic nitrogen-containing ligand of ruthenium or osmium reagent and a series of known β-lactam hydrolysis pattern spectrum as standards for comparison with the empirically generated hydrolysis pattern spectrum which permits the identification of the β-lactam.

28. A kit according to claim 1 for identification of bacteria which comprises a sufficient number of unit dosage amounts of different β-lactams to perform a series of assays to generate a spectrum of empirically derived hydrolysis patterns, and corresponding premeasured amounts of a bidentate aromatic heterocyclic nitrogen-containing ligand of ruthenium or osmium reagent and a series of β-lactam hydrolysis pattern spectrum for known bacteria as standards for comparison with the empirically generated hydrolysis pattern spectrum which permits identification of the bacteria.

29. A method for identifying β-lactams comprising,
   (a) preparing a series of samples containing a β-lactam of interest from a sample source;
   (b) contacting the series of samples containing the β-lactam of interest with a bidentate aromatic heterocyclic nitrogen-containing ligand of ruthenium or osmium reagent and a series of different β-lactamases;
   (c) subjecting each of contacted samples of step (b) to conditions which result in electrochemiluminesence;
   (d) separately measuring the resulting electrochemiluminescence for each sample of the series to obtain a series of base-line readings;
   (e) incubating the series of samples of step (d);
   (f) subjecting the incubated samples of step (e) to conditions which result in electrochemiluminesence;
   (g) separately measuring the resulting chemiluminescence for each incubated sample and comparing it to the base-line reading for the corresponding sample in the series to determine the presence of a difference in the measured values;
   (h) generating a spectrum of differences in measured values for the series; and
   (i) comparing the generated spectrum with a standard spectrum to identify the β-lactam present in the source material.

30. A method for identifying bacteria comprising,
   (a) preparing a series of samples containing the bacteria of interest from a sample material;
   (b) contacting a series of samples suspected of containing the same bacteria with a bidentate aromatic heterocyclic nitrogen-containing ligand of ruthenium or osmium reagent and a series of different β-lactams;
   (c) subjecting each of the contacted sample of step (b) to conditions which result in electrochemiluminesence;
   (d) measuring the resulting electrochemiluminescence to obtain a base-line reading for each of the samples in the series;
   (e) incubating the series of samples of step (d);
   (f) subjecting the incubated samples of step (e) to conditions which result in electrochemiluminesence;

(g) measuring the resulting chemiluminescence for each sample in the series and comparing it to the corresponding base-line value for the same sample in the series to determine the presence of a difference in measured values;

(h) generating a spectrum of differences in measured values for the series; and (i) comparing the generated spectrum with a spectrum standard to identify the bacteria in the source material.

31. A method for identifying bacteria according to claim 30 wherein the series of different β-lactams includes both cephalosporins and penicillins.

* * * * *